US010870087B2

(12) United States Patent
Olivier et al.

(10) Patent No.: US 10,870,087 B2
(45) Date of Patent: Dec. 22, 2020

(54) MEMBRANE SUPPORT AND MEMBRANE FILTRATION DEVICE

(71) Applicant: MERCK PATENT GMBH, Darmstadt (DE)

(72) Inventors: Stephane Olivier, Rosheim (FR); Didier Metz, Stotzheim (FR)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/779,343

(22) PCT Filed: Nov. 4, 2016

(86) PCT No.: PCT/EP2016/001832
§ 371 (c)(1),
(2) Date: May 25, 2018

(87) PCT Pub. No.: WO2017/088951
PCT Pub. Date: Jun. 1, 2017

(65) Prior Publication Data
US 2018/0318772 A1 Nov. 8, 2018

(30) Foreign Application Priority Data
Nov. 27, 2015 (EP) ..................................... 15290294

(51) Int. Cl.
*B01D 69/10* (2006.01)
*C12M 1/12* (2006.01)
(Continued)

(52) U.S. Cl.
CPC ................ *B01D 69/10* (2013.01); *A61L 2/28* (2013.01); *B01L 3/00* (2013.01); *C12M 25/02* (2013.01);
(Continued)

(58) Field of Classification Search
CPC ....... A61L 2/28; B01D 2313/12; B01D 61/14; B01D 69/10; B01L 2200/10; B01L 3/00; C12M 25/02; C12M 37/02; C12Q 1/22
See application file for complete search history.

(56) References Cited

U.S. PATENT DOCUMENTS 4,036,698 A     7/1977   Bush
4,159,954 A *   7/1979   Gangemi ............. B01D 29/012
                                                         128/205.29
(Continued)

FOREIGN PATENT DOCUMENTS

EP           493499 A1    7/1992
GB          2330088 A    4/1999
(Continued)

OTHER PUBLICATIONS

International Search Report PCT/EP2016/001832 dated Feb. 1, 2017.
(Continued)

*Primary Examiner* — Pranav N Patel
(74) *Attorney, Agent, or Firm* — Millen, White, Zelano & Branigan, PC; Ryan Pool

(57) ABSTRACT

A membrane support, usable for example in a membrane filtration device, comprises a support surface provided on an upstream side of the membrane support and adapted to support a flat filtration membrane thereon, and a drainage structure arranged below the support surface to collect a fluid that has passed the filtration membrane supported on the support surface and guide the fluid away to a downstream side, wherein the support surface has a plurality of recesses distributed over the support surface and formed to absorb expansions of the filtration membrane. The membrane support avoids fold formation of a membrane due to membrane expansion after hydration.

20 Claims, 3 Drawing Sheets

(51) Int. Cl.
    *A61L 2/28*         (2006.01)
    *C12Q 1/22*        (2006.01)
    *B01L 3/00*        (2006.01)
    *B01D 61/14*       (2006.01)
    *B01D 69/06*       (2006.01)

(52) U.S. Cl.
    CPC ............... *C12M 37/02* (2013.01); *C12Q 1/22*
        (2013.01); *B01D 61/14* (2013.01); *B01D 69/06*
        (2013.01); *B01D 2313/12* (2013.01); *B01L*
        *2200/10* (2013.01)

(56) References Cited

U.S. PATENT DOCUMENTS

| | | | |
|---|---|---|---|
| 4,640,777 A | | 2/1987 | Lemonnier |
| 5,269,917 A | * | 12/1993 | Stankowski ......... B01D 29/012 |
| | | | 156/73.1 |
| 5,792,354 A | * | 8/1998 | Aksberg ............... B01D 29/012 |
| | | | 210/321.75 |
| 2003/0057148 A1 | * | 3/2003 | Zuk, Jr. ................. B01D 29/05 |
| | | | 210/445 |
| 2010/0288691 A1 | * | 11/2010 | Shigesada ............. B01D 69/10 |
| | | | 210/455 |

FOREIGN PATENT DOCUMENTS

| | | |
|---|---|---|
| WO | 2013070730 A2 | 5/2013 |
| WO | 2015095145 A1 | 6/2015 |

OTHER PUBLICATIONS

European Pharmacopoeia 5.0 section 2.6.1 Sterility dated Jan. 2005 (p. 145).

\* cited by examiner

MEMBRANE SUPPORT AND MEMBRANE FILTRATION DEVICE

The invention concerns a membrane support, usable for example in a membrane filtration device, and a membrane filtration device using the membrane support.

Membrane filtration devices are known and frequently used as sample preparation devices, preferably for sterility and bio-burden testing, for example applicable for testing purposes in connection with the control of manufacturing processes or for final product testing in the pharmaceutical, biopharmaceutical, biotech, hospital, food and beverage industries but also for diagnostic, health care and research for particles and biological elements.

Sterility or bio-burden testing processes require a sample preparation method that involves specific consumables, hardware and sample preparation steps and the method is known as a standardized method throughout the industry. In the growth based sterility testing the sample preparation involves promoting the growth of any micro-organisms to be detected by a direct contact of liquid nutrition media that is introduced above or under a calibrated membrane filter that retains the micro-organisms and by incubating the container with the filter membrane and nutrition media at a predetermined temperature. Turbidity changes of the nutrition media indicate the presence of micro-organisms. Alternately, micro-organisms can be visually detected on the membrane filter.

The equipment and sample preparation steps of the sample preparation for such sterility and bio-burden testing includes the following typical steps:

1. Pre-Wetting

The pre-wetting is used to saturate the porosity of the membrane filter with the right rinsing buffer in order to avoid or reduce the risk of molecule binding to the membrane filter, mostly in case of antibiotic sterility testing. Such a process is described, for example, in European Pharmacopoeia 5.0, 2.6.1 Sterility.

For sterility testing, a container with the buffer solution, i.e. a bottle, is connected to sample preparation devices (membrane filtration devices) like the one described in U.S. Pat. No. 4,036,698 A, typically with a peristaltic pump located in a fluid connection between the buffer solution container and the sample preparation devices and the buffer solution is pumped through the sample preparation devices.

For Bioburden testing, the buffer solution is poured in an open filtration device.

This step is to be repeated on each of two or more sample preparation devices for each testing task.

2. Sample Filtration

This step is used to concentrate the micro-organisms on the surface of the membrane filter in the sample preparation devices.

For sterility testing a container, i.e. a bottle or syringe, with a sample fluid is connected with the sample preparation devices typically via the peristaltic pump. This step needs to be performed simultaneously on each of two or more sample preparation devices with a perfect equal splitting of the sample transfer and filtering through the respective sample preparation devices. For bioburden testing, the sample fluid is poured in an open filtration device.

3. Rinsing

This step is used to rinse all tubing, the internal walls of the sample preparation device or container to ascertain that all the micro-organisms are collected at the surface of the membrane filter. In this step, the porosity of the membrane filter is rinsed in order to remove any inhibitor which may delay or prevent the growth development of potential contaminants (micro-organisms).

For sterility testing, this step, too, requires to connect a container, i.e. a bottle, with a rinsing fluid to the sample preparation devices typically via the peristaltic pump and to achieve the desired fluid flow through the volume of the devices. This step, too, has to be performed on each of the two or plural sample preparation devices.

For bioburden testing, the rinsing fluid is poured in an open filtration device.

4. Growth Media Addition

For sterility testing this step is used to bring the right volume of nutriments (aerobic or anaerobic) into each of the sample preparation devices above the membrane filter. A nutrition media container is connected to the sample preparation devices and the right volume is measured and the sample preparation devices are closed at the end of the step. This step is to be typically performed with one of the sample preparation devices with the aerobic media and then on another sample preparation device with the anaerobic media.

For bioburden testing the membrane can either be transferred on a solid agar media cassette, or a liquid media can be inserted under the membrane.

5. Incubation

In this step, the single, two or more sample preparation devices or containers are incubated under the specific incubation conditions for optimum growth development. The incubation is performed separately for the sample preparation devices or containers with the aerobic and anaerobic media.

6. Reading

For sterility testing turbidity changes or local development of colonies on the filter membranes or filaments in the fluid are detected by regular reading, either by the naked eyes or by automated optical inspection technologies, to review and detect micro-bio-growth during the predetermined incubation term.

For bioburden testing local development of colonies on the filter membranes are detected by regular reading, either by the naked eyes or by automated optical inspection technologies.

7. Identification

For sterility testing, in case of a positive detection of a sample a liquid is extracted from the sample preparation device or container using a syringe or the like and further analysis is subsequently performed.

For bioburden testing colony can be extracted from the sample preparation device or container using an oese or the like and further analysis is subsequently performed.

The above-mentioned steps are typical for sterility testing and for bioburden testing and a plurality of sample preparation devices have been developed for this process.

WO 2013/070730 A2, for example, discloses a sample preparation or cell culturing device (i.e. a membrane filtration device within the meaning of this application) for sterility testing. The device has a housing that contains a lid having an optically clear window, a fluid distribution channel, a sample injection port fluidically connected to the fluid distribution channel, a base that comprises a porous media pad of sintered polyethylene with a flat support surface on which a filter membrane is to be placed, and a media injection port located on the bottom of the base fluidically connected to the media pad. The porous media pad serves as a drainage structure in this case to collect a fluid that has passed the filter membrane supported on the support surface thereof. The lid mates to the base to form a sterile seal for a first chamber and the distribution channel is disposed above the media pad. A sample fluid introduced into the fluid distribution channel through a sample injection port in the lid is distributed evenly to the media pad.

Some membrane filter materials used in these devices and processes are very sensitive to humidity and can have significant swelling expansion depending on the hygrometry. Expansion of the membrane can occur during storage, manufacturing or during the filtration process.

If the membrane is a flat disk, which is common, the membrane disk will increase its diameter. For a standard disk with a diameter of 40 mm, for example, a diameter increase can be more than 0.15 mm depending on the filter material. Parameters of influence are the thickness, the porosity, the process conditions and the formulation of the membrane material. For some applications the membrane disk is integrated in the device and the external periphery of the membrane disk needs to be firmly held or bounded. In this case the increase of the membrane surface may generate a fold or a bump after hydration when placed on a flat support surface such as an agar media surface because the external periphery cannot move and compensate the excess membrane surface. On the membrane disk with a diameter of 40 mm (which has an original surface area of 1256.6 $mm^2$) referred to as an example the surface area expanded by 11 $mm^2$ can cause a bulge or fold with a deflection from the support surface of 1.7 mm. Examples of folds created in such a situation are shown in FIG. 1.

Any fold on the membrane can, however, have an impact on the bacterial growth and colony morphology due to media access, capillarity, air bubble inclusion between the membrane and the agar media. A fold can also have a negative impact on the visual or optical reading reproducibility.

One existing solution to cope with the problem is the use of rigid fritted or grid material for the membrane support and placing the flat membrane on the flat membrane support surface thereof which has a slightly raised peripheral step. After hydration the excess membrane material is compensated in that the membrane can slip over the peripheral step. The edge of the step can, however, leave a visible mark on the membrane and the contact between the membrane and the agar can be locally lost. Also, the fritted material may be more difficult to rinse, especially in case of filtration of matrices containing inhibitors, and may impact the bacterial growth. In case very foaming samples are processed the fritted material may increase the foam formation in the waste bottle with a negative impact on the maximum volume that can be filtered and the accuracy of the reading result of level detection sensors in the bottle. In case of disposable porous fritted material the gamma sterilization may create free radicals which can impact the growth of micro-organisms on the membrane.

Another existing solution is the use of a membrane support with a concave support surface having a low point at the central portion of the support. In this case the dry membrane is not fully supported in the central portion and at the intermediate periphery which creates the risk of membrane breakage during manufacturing and assembly, shipment and at an early stage of the filtration process. While the membrane expansion after hydration can be compensated and fold formation can be avoided provided the membrane is kept close to the support surface of the concave support, a problem may exist if the concave filter after filtration is transferred onto a flat surface because air bubbles may be trapped under the membrane which could cause local membrane drying.

A still further existing solution consists of placing an elastic supporting pad between the membrane and the drainage structure of the membrane support. Although the deformation of the elastic pad under the differential of pressure during filtration can avoid the fold creation in the membrane during the liquid filtration, the membrane expansion is evenly distributed over the entire surface of the membrane and can create a dome-shape nevertheless. Further, as in the case of using a fritted material, the pad material may be more difficult to rinse, especially in case of filtration of matrices containing inhibitors, and may impact the bacterial growth, or, in case very foaming samples are processed, the pad material may increase the foam formation in the waste bottle with a negative impact on the maximum volume that can be filtered and the accuracy of the reading result of level detection sensors in the bottle. In case of disposable porous pad material the gamma sterilization may create free radicals which can impact the growth of micro-organisms on the membrane. Finally, the presence of the pad under the membrane can increase the flow resistance and increase the filtration time.

It is an object of the present invention to provide a membrane support, usable for example in a membrane filtration device, which avoids fold formation of a membrane due to membrane expansion after hydration and at least some of the other disadvantages in the art. The present invention intends to also provide a membrane filtration device using the membrane support.

To solve the problem, the present invention provides a membrane support as defined in claim 1, and a membrane filtration device as defined in claim 15. Preferred embodiments of the membrane support and of the membrane filtration device are defined in the dependent claims.

The membrane support of the invention comprises a support surface provided on an upstream side of the membrane support and adapted to support a flat filtration membrane thereon, and a drainage structure arranged below the support surface to collect a fluid that has passed the filtration membrane supported on the support surface and guide the fluid away to a downstream side, wherein the support surface has a plurality of recesses distributed over the support surface and formed to absorb expansions of the filtration membrane.

The plurality of small recesses formed in the support surface of the membrane and distributed over it allows the membrane to be supported evenly and substantially throughout its entire surface in a dry state (i.e. during manufacturing and shipping) and it allows the expansion of the membrane after hydration to be evenly distributed over the surface of the membrane even if the periphery of the membrane is firmly held or bounded in that the material may expand into the plural shallow recesses all over the surface area of the membrane. Thus, the contact between the membrane and the agar during use of the membrane support in a filtration process is maximized and trapping of bubbles under membrane is avoided. Further, the media diffusion through the membrane pores by capillary action is improved.

This yields remarkable advantages when the membrane support is used in a membrane filtration device during filtration because the membrane expansion is possible despite of the membrane being held at its peripheral edge, it ensures the desired membrane pressure differential during the filtration process, it allows sufficient drainage during the filtration process, and it avoids the forming of folds or bulges in the membrane.

As a further advantage the foam formation is avoided or at least reduced even in case very foaming samples are processed, and the rinsing performance specifically for antibiotic testing is improved, for example as compared to the use of elastic pads which require several rinsing steps.

During incubation after filtration the formation of folds is avoided when the membrane is transferred on agar nutrition medium and it provides good growth conditions and uniform access of nutriments to any point of the membrane due to the intimate, bubble-free contact between the membrane and the agar.

Preferably, the recesses thus have a depth from a peak at the support surface to a bottom and a width selected such that, upon deformation of the membrane supported on the support surface during filtration, contact between the membrane and the support surface is maintained.

Preferably, the ratio of depth to width of the recesses is from 5 to 40, preferably from 20 to 40 or from 10 to 20 or from 5 to 10.

Preferably, the recesses have curved transitions from the support surface and preferably from the bottom.

Preferably, the recesses are regularly/periodically or irregularly formed in the radial and/or the circumferential direction of the support surface.

Preferably, the recesses are sinusoidal in cross section.

Preferably, the recesses are continuous and/or discontinuous.

Preferably, the recesses comprise annular grooves, preferably concentric grooves, and/or dimples.

Preferably, the drainage structure comprises a channel network connected with a drainage port on the downstream side of the membrane support.

Preferably, the channels of the network are formed so as to avoid dead legs with respect to a flow direction towards the drainage port.

Preferably, the channels of the network extend radially from the drainage port and or circumferentially of the drainage port and/or a bottom of the channels rises continuously in a height direction from the drainage port when the membrane support is held in a posture with the support surface being horizontal, wherein the drainage port is preferably centered with respect to the support surface.

Preferably, the membrane support has a peripheral membrane edge holding feature which can be, for example, a clamp or a step-like structure rising above the support surface.

In a preferred example embodying the membrane support for use with a mixed cellulose filtration membrane, the width of the recesses is about 1 mm and the depth of the recesses from the support surface is in a range of 0.05 mm to 0.4 mm, preferably 0.2 mm, and more preferably 0.1 mm.

A membrane filtration device of the invention comprises a membrane support according to the invention, wherein a filtration membrane is preferably placed on the membrane support surface, a liquid reservoir located upstream of the support surface of the membrane support, and a discharge port communicating with the downstream side of the support surface.

BRIEF DESCRIPTION OF THE DRAWINGS

Preferred embodiments of the membrane support of the invention will be described by reference to the attached drawing, in which.

Figure 1:
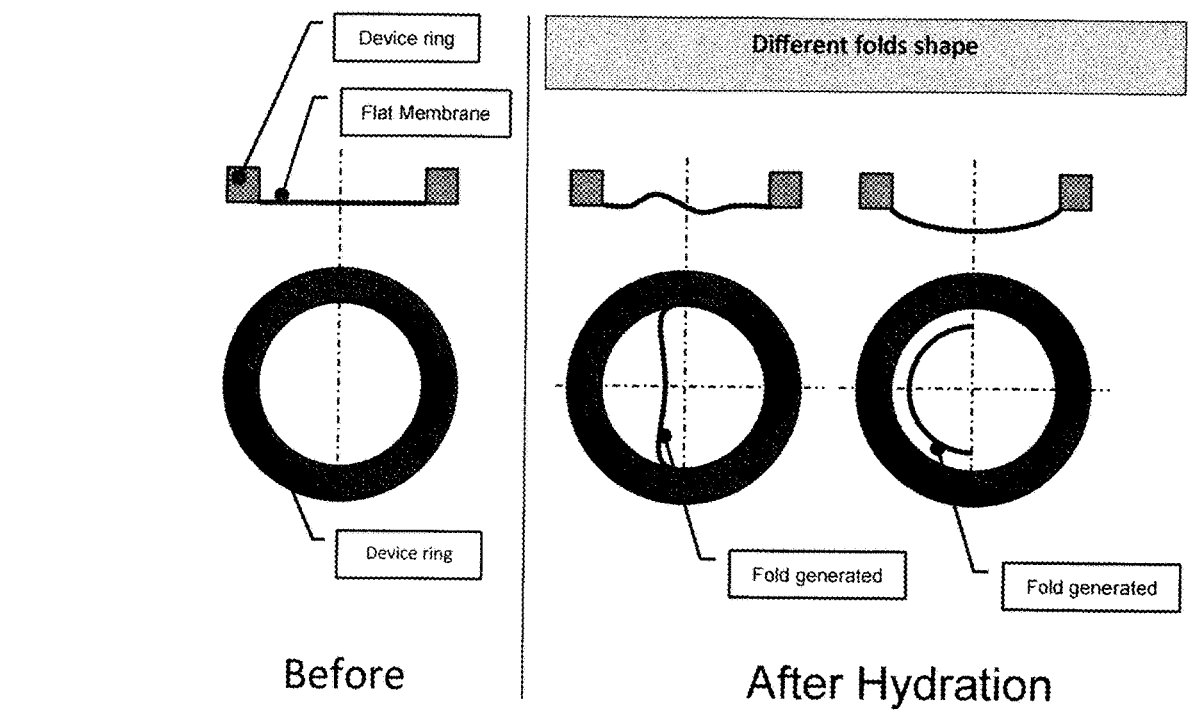
FIG. 1 shows the situation of fold formation in a membrane on a membrane support in the prior art.
Figure 2:
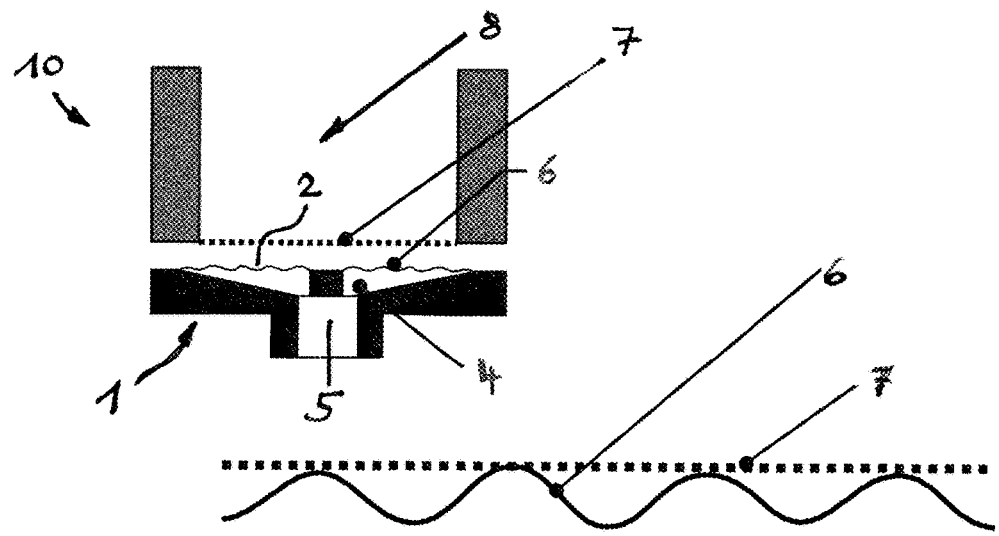
FIG. 2 shows a schematic and out-of scale representation of a membrane filtration device and of a membrane support according to the invention.

A membrane filtration device and a membrane support according to the invention is shown in a very schematic and out-of scale representation in FIG. 2. The membrane support 1 of the invention comprises a support surface 2 adapted to support a flat filtration membrane 7 and provided on an upstream side of the membrane support 1 with respect to an envisaged flow direction of a fluid to be filtered through the membrane to be supported on the support. A drainage structure 4 is arranged below the support surface 2 to collect the fluid that has passed the filtration membrane 7 supported on the support surface 2 and guide the fluid away to a downstream side.

The membrane support 1 is intended to be arranged in a membrane filtration device 10 which may include the filtration membrane 7 placed on the membrane support surface in a manufactured state or may be adapted to receive the membrane at the point of use. The membrane filtration device 10 also has a liquid reservoir 8 in the form of a closed or closable chamber located upstream of the support surface 2 of the membrane support 1, and a discharge port 5 communicating with the downstream side of the support surface. The discharge port 5 may be part of the filtration device 10 or of the membrane support 1. One or more inlet(s) to the liquid reservoir and additional chambers for holding, for example, a substance required for the sample preparation process, may be provided as known in the art but are not shown. Also, a top side of the chamber 8 is sealingly closed or can be closed by a transparent lid or cover to allow inspection of the membrane placed on the support to monitor the sample and process.

The lower part of FIG. 2 shows a magnified representation of the membrane support surface 2 of the membrane support 1 in a cross section. As is visible the support surface is provided with a plurality of small recesses 6 which are—although not shown—distributed over substantially the entire support surface. These recesses, which are indented or formed to recede from a top reference plane defined by the peaks or apexes of the resulting recess pattern, are formed and dimensioned to absorb expansions of the filtration membrane placed in the reference plane.

It will be appreciated that the peaks or apexes of the support surface allow the membrane to be supported evenly and substantially throughout its entire surface in a dry state (i.e. during manufacturing and shipping) and it allows the expansion of the membrane after hydration to be evenly distributed over the surface of the membrane even if the periphery of the membrane is firmly held or bounded in that the material may expand into the plural shallow recesses all over the surface area of the membrane. The depth of the recesses and their width is apparently much smaller than that of the channels 4 typically forming the drainage structure for the fluid having passed the membrane. In fact, the recesses can be considered as being imparted or overlaid on a traditional continuous support surface in which the larger drainage channels are formed.

The recesses 6 thus have a depth from the peak at the support surface to the bottom and a width selected such that, upon deformation of the membrane supported on the support surface during filtration, contact between the membrane and the support surface is maintained. Depending on the membrane material (i.e. its expansion tendency and elasticity or rigidity) and its thickness the relation between the depth and width of the recesses is preferably from 5 to 40, preferably from 20 to 40 or from 10 to 20 or from 5 to 10. Any ratio within these sub-ranges is envisaged and it is independent from the diameter or size of the membrane used with the support and the actual profile of the recesses in cross section.

In a preferred example embodying the membrane support for use with a mixed cellulose filtration membrane, the width of the recesses is about 1 mm and the depth of the recesses from the top plane of the support surface where the filter membrane will be located in the dry state is in a range of 0.05 mm to 0.4 mm, preferably 0.2 mm, and more preferably 0.1 mm.

Figure 3:
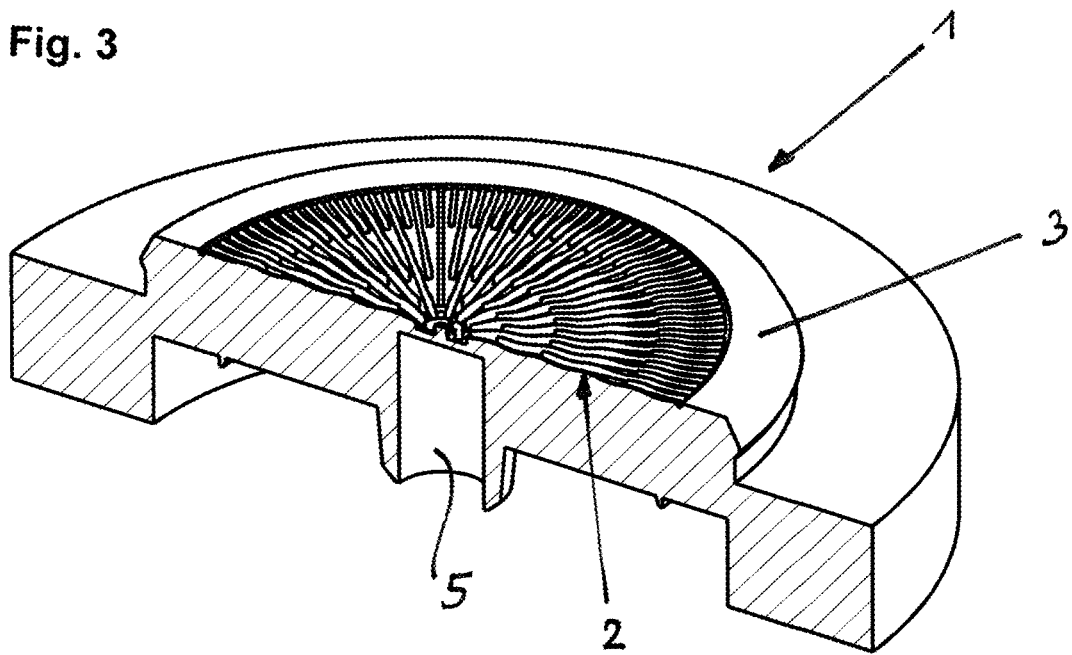
FIG. 3 shows a cross section view of a membrane support according to an embodiment of the present invention.
Figure 4:
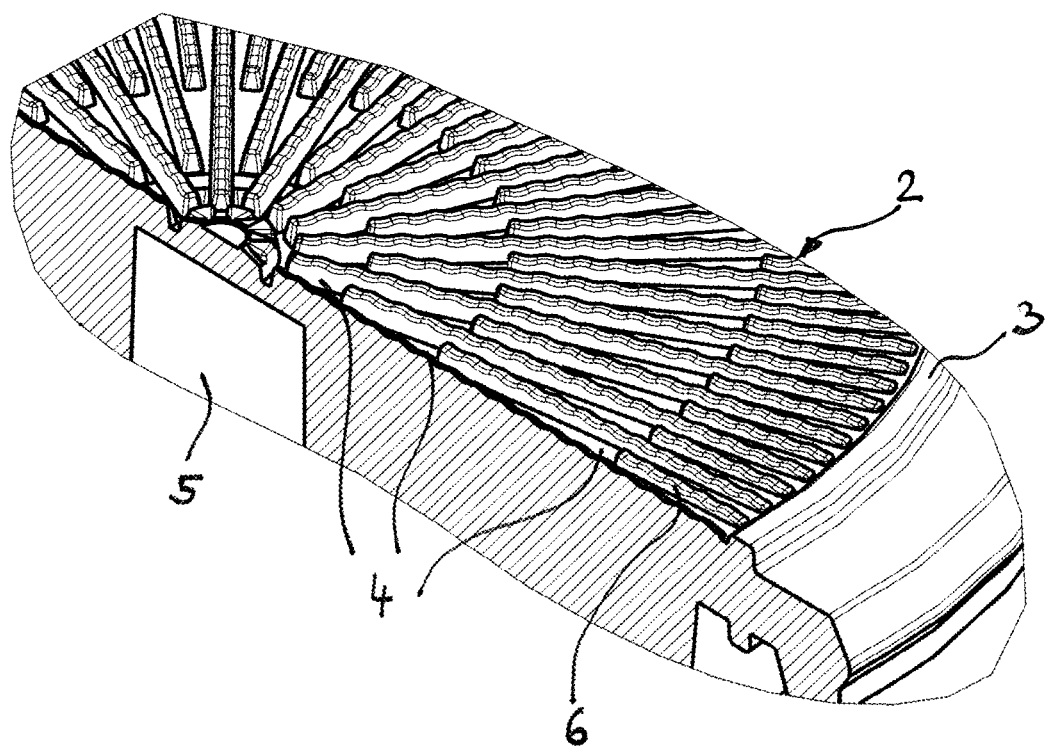
FIG. 4 shows an enlarged view of a portion of the membrane support of FIG. 3.

The FIG. 3 shows a cross section view of a membrane support according to an embodiment of the present invention and the FIG. 4 shows an enlarged view of a central portion of the membrane support of FIG. 3. The channels 4 of the drainage structure form a channel network arranged to guide and direct the fluid having passed the membrane surface towards a drainage port 5 on the downstream side of the membrane support 2. In this case the channels 4 forming the channel network extend radially from the drainage port 5 and, in order to maintain a constant flow of fluid towards the port 5 and to avoid dead legs with respect to a flow direction towards the drainage port, the bottom of the channels 4 rises continuously in a height direction from the drainage port 5 when the membrane support is held in a posture with the support surface being horizontal, to the outer periphery. The drainage port is preferably centered with respect to the support surface but this is not mandatory.

Due to the drainage channels 4 being formed radially the support surface is formed by raised lands or ridges and the small recesses 6 are formed in the top surfaces of the lands to also extend in a sinusoidal profile in the radial direction, wherein the peaks and bottoms are aligned in the circumferential direction to also form concentric wave patterns. In order to avoid overstressing of the membrane and limit the deformation of the membrane into the drainage channels the width of the drainage channels 4 should be minimized so that, at the same time, the surface area supporting the membrane during filtration is enlarged. In this way the membrane support does not require any additional supporting structure such as a net, mesh, fritted material, woven or non-woven materials in the support surface.

In an alternative design—but also in combination with the radial drainage channels as shown—the drainage channels or further drainage channels could be formed circumferentially to connect the radial channels or to spirally lead towards the drainage port.

A rim 3 is optionally formed so as to extend about the external periphery of the membrane support surface 2 and so as to be raised above the surface in order to define a step-like structure serving as a boundary for the movement and/or expansion of the membrane disk. This raised rim is thus a form of a peripheral membrane edge holding feature which can alternatively be, for example, a clamp or another mechanical constraint or holder for the membrane.

The recesses in the preferred embodiment shown in the figures have curved and continuous smooth transitions from the peaks at the top support level of the support surface to the slopes and from the slopes to the bottom. A profile with a sinusoidal cross section is thus preferred.

The recesses can be machined into a base surface of the membrane support or can be integrally molded when the support is formed, for example from plastics material.

Figure 5:
FIG. 5 shows a cross section profile of recesses of a membrane support according to the invention.

If the plurality of recesses are consecutively and continuously arranged in a sinusoidal wave profile in cross section along the extension direction as shown in FIG. 5 the number of periods of the wave, the amplitude A of the wave (depth of the recesses from peak to bottom), the period T of the wave (the width of the recesses or the peak-to-peak spacing), the surface area of the membrane disk after hydration and expansion, and the absorbed surface expansion is summarized for an exemplary membrane disk with a diameter of 40 mm and a nominal flat surface of 1256.6 mm² as follows:

| Number of periods | Amplitude A (depth) (mm) | Period T (width) (mm) | Surface area (mm²) | Absorbed surface (mm²) | Ratio T/A |
|---|---|---|---|---|---|
| 5 | 0.1 | 4 | 1259 | 2.5 | 40 |
| 10 | 0.05 | 2 | 1259 | 2.5 | 40 |
| 5 | 0.2 | 4 | 1265 | 8.5 | 20 |
| 10 | 0.1 | 2 | 1265 | 8.5 | 20 |
| 20 | 0.05 | 1 | 1265 | 8.5 | 20 |
| 5 | 0.4 | 5 | 1290 | 33.5 | 10 |
| 10 | 0.2 | 2 | 1290 | 33.5 | 10 |
| 20 | 0.1 | 1 | 1290 | 33.5 | 10 |

Based on the table above one will appreciate that different combinations of number of periods, amplitude and period can compensate and absorb approximately the same surface expansion.

Figure 6:
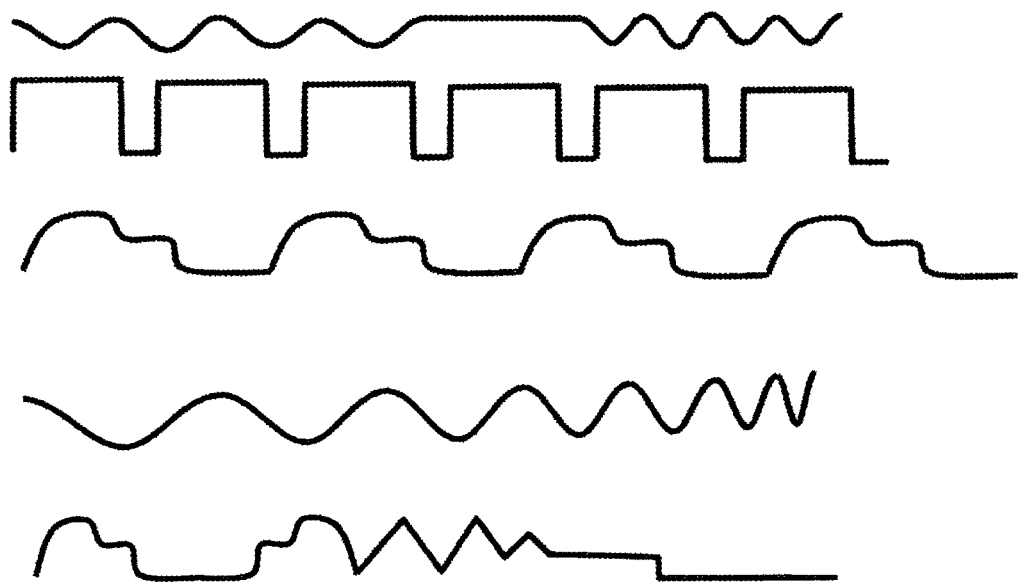
FIG. 6 shows various alternative cross section profiles of membrane support surfaces according to the invention.

The support surface profile and the form of the recesses is not limited to a regular sinusoidal profile in cross section. Other regularly/periodically or irregularly formed profiles which may extend in the radial and/or the circumferential direction of the support surface so as to cover substantially the entire active support area are possible. FIG. 6 shows a number of exemplary alternative cross section profiles in the extension direction (the radial or the circumferential direction) of membrane support surfaces according to the invention. The irregularity may be in the period (width), the amplitude (depth), the number of periods or recesses and/or the shape of the individual recesses.

In a further alternative the recesses may be individual dimples or indentations from the support surface distributed in various patterns about the support surface or annular grooves, preferably concentric grooves, or combinations thereof.

The invention claimed is:

1. A membrane support (1), comprising
a support surface (2) provided on an upstream side of the membrane support and adapted to support a flat deformable filtration membrane (7) thereon, and
a drainage structure (4) arranged below the support surface (2) to collect a fluid that has passed the deformable filtration membrane (7) supported on the support surface (2) and guide the fluid away to a downstream side, wherein the drainage structure (4) comprises a channel network connected with a drainage port (5) on the downstream side of the membrane support (1),
wherein the support surface (2) is formed by raised lands or ridges and has a plurality of recesses (6) distributed over the support surface (2), wherein the depth and width of the recesses is smaller than that of the channels and formed to absorb expansions of the deformable filtration membrane (7), wherein the ratio of depth to width of the recesses (6) is from 5 to 40,
wherein the deformable filtration membrane (7) has an absorbed surface area of at least 8.5 mm² of a total nominal flat surface area of 1256.6 mm².

2. The membrane support (1) according to claim 1, wherein the recesses (6) have curved transitions at the support surface (2).

3. The membrane support (1) according to claim 1, wherein the recesses (6) are regularly/periodically or irregularly formed in the radial and optionally the circumferential direction of the support surface (2).

4. The membrane support (1) according to claim 3, wherein the recesses (6) are sinusoidal in cross section.

5. The membrane support (1) according to claim 1, wherein the recesses (6) are continuous or optionally discontinuous.

6. The membrane support (1) according to claim 1, wherein the recesses (6) comprise annular grooves.

7. The membrane support (1) according to claim 1, wherein the channels of the channel network are formed so as to avoid dead legs with respect to a flow direction towards the drainage port (5).

8. The membrane support (1) according to claim 1, wherein the channels of the channel network extend radially from the drainage port (5) and/or circumferentially of the drainage port (5) and optionally a bottom of the channels rises continuously in a height direction from the drainage port (5) when the membrane support is held in a posture with the support surface (2) being horizontal.

9. The membrane support (1) according to claim 1, wherein the membrane support (1) has a peripheral membrane edge holding feature.

10. The membrane support (1) according to claim 9, wherein the membrane holding feature comprises a step (3) rising above the support surface (2).

11. The membrane support (1) according to claim 1, wherein, the width of the recesses (6) is about 1 mm and the depth of the recesses from the support surface is in a range of 0.05 mm to 0.4 mm.

12. A membrane filtration device (10) comprising
a membrane support (1) according to claim 1, wherein a deformable filtration membrane (7) is placed on the membrane support surface (2);
a liquid reservoir (8) located upstream of the support surface (2) of the membrane support (1); and
a discharge port (5) communicating with the downstream side of the support surface (2),
wherein the deformable filtration membrane (7) has an absorbed surface area of at least 8.5 mm² of a total nominal flat surface area of 1256.6 mm².

13. The membrane support (1) of claim 1, wherein the ratio of width to depth of the recesses (6) is from 20 to 40.

14. The membrane support (1) of claim 1, wherein the ratio of width to depth of the recesses (6) is from 10 to 20.

15. The membrane support (1) of claim 1, wherein the ratio of width to depth of the recesses (6) is from 5 to 10.

16. The membrane support (1) of claim 2, wherein the recesses (6) have curved transitions at the bottom.

17. The membrane support (1) of claim 6, wherein the recesses (6) comprise concentric grooves and optionally dimples.

18. The membrane support (1) of claim 8, wherein the drainage port (5) is centered with respect to the support surface (2).

19. The membrane support (1) of claim 11, wherein the depth of the recesses from the support surface is 0.2 mm.

20. The membrane support (1) of claim 11, wherein the depth of the recesses from the support surface is 0.1 mm.

* * * * *